United States Patent [19]
Rocklage et al.

[11] Patent Number: 5,190,744
[45] Date of Patent: Mar. 2, 1993

[54] METHODS FOR DETECTING BLOOD PERFUSION VARIATIONS BY MAGNETIC RESONANCE IMAGING

[75] Inventors: Scott M. Rocklage, Los Gatos; John Kucharczyk, Mill Valley; Michael E. Moseley, San Francisco, all of Calif.

[73] Assignees: Salutar, Sunnyvale; The Regents of the University of Ca., Oakland, both of Calif.

[21] Appl. No.: 490,859

[22] Filed: Mar. 9, 1990

[51] Int. Cl.⁵ .................. G01N 24/08; A61K 31/555; G01V 3/00
[52] U.S. Cl. .................................... 424/9; 436/173; 514/184; 514/492; 514/836; 128/653.3; 128/653.4; 324/306; 324/309
[58] Field of Search ............................ 424/9; 436/173; 514/492, 184, 836; 324/306, 309; 128/653 AF, 653 CA, 654

[56] References Cited

U.S. PATENT DOCUMENTS

| | | | |
|---|---|---|---|
| 4,532,473 | 7/1985 | Wehrli | 324/306 |
| 4,639,365 | 1/1987 | Sherry | 424/9 |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,777,956 | 10/1988 | Malcovski | 128/653 AF |
| 4,800,889 | 1/1989 | Dumoulin et al. | 128/653 AF |
| 4,836,209 | 6/1989 | Nishimura | 128/653 AF |
| 4,849,697 | 7/1989 | Cline et al. | 324/306 |
| 4,862,080 | 8/1989 | Van As | 324/306 |
| 4,915,933 | 4/1990 | Matwiyoff | 424/9 |
| 4,947,837 | 8/1990 | Sano et al. | 128/653 AF |

FOREIGN PATENT DOCUMENTS

| | | |
|---|---|---|
| 87/76217 | 2/1988 | Australia . |
| 88/10649 | 7/1988 | Australia . |
| 88/14611 | 10/1988 | Australia . |
| 1253514 | 5/1989 | Australia . |
| 186947 | 7/1986 | European Pat. Off. . |
| 230893 | 8/1987 | European Pat. Off. . |
| 232751 | 8/1987 | European Pat. Off. . |
| 292689 | 11/1988 | European Pat. Off. . |
| 299795 | 1/1989 | European Pat. Off. . |
| 85/04330 | 10/1985 | PCT Int'l Appl. . |
| 88/00060 | 1/1988 | PCT Int'l Appl. . |
| 89/06979 | 8/1989 | PCT Int'l Appl. . |
| 89/09625 | 10/1989 | PCT Int'l Appl. . |

OTHER PUBLICATIONS

Cacheris et al., SMRM 8, Aug. 1988, Works in Progress.
Belliveau et al., SMRM 8, Aug. 1988, p. 222.
Lauffer, CMR '89, Oct. 1989, MR1.
Rocklage et al., CMR '89, Oct. 1989, MR3.
Stringer et al., J. Comp. Assist Tomogr. 13:386–394 (1989).
Moonen et al., Science 250:53–61 (Oct. 1990).
Ell et al., The Lancet, Mar. 25, 1989, pp. 665–666 (1989).
Amersham, "Ceretec-Technetium HM-PAO agent for rCBF scintigraphy-meeting the challenge of the blood brain barrier" (1989).
Ell et al., Nuclear Medicine Communications 6:437–441 (1985).
Nowotnik et al., Nuclear Medicine Communications 6:499–506 (1985).
Moseley et al., Magn. Reson. Med. 14:330–346 (1990).
Detre et al., Magn. Reson. Med. 14:389–395 (1990).
Le Bihan et al., Magn. Reson. Med. 14:283–292 (1990).
Le Bihan et al., Magn. Reson. Med. 10:324–337 (1989).
Sarker et al., SMRI '90, paper No. 302 (1990).
Belliveau et al., Magn. Reson. Med. 14:538–546 (1990).
Rosen et al., Magn. Reson. Med. 14:249–265 (1990).
Rosen et al., Magnetic Resonance Quarterly 5:263–281 (1989).
Lauffer, Invest. Radiol. 25:S32–S33 (1990).
Cacheris et al., RSNA '88, paper/poster No. 1266 (1988).
Moseley et al., SMRM 9, (Aug. 1989) p. 43.
Moseley et al., RSNA '89, paper/poster No. 1192 (1989).
Frank et al., ASMR (1990).
Saeed et al., RSNA (1988).
Saeed et al., SMRM 9, Aug. 1989, 356.
Saeed et al., SMRM 9, Aug. 1989, 674.
Wendland et al., American Heart Association, 13–16 Nov. 1989.
Higgins et al., CMR, Oct. 1989, MR26.
Saeed et al., RSNA '89, paper/poster No. 1094 (1989).
Carvlin et al., SMRI-1989.
Villringer et al., Magn. Reson. Med. 6:164–174 (1988).
Moseley et al., AJNR 11:423–429 (1990).
Lauffer, Mag. Reson. Quarterly 6:65–84 (1990).
Yonas et al., Radiology 152:435–42 (1984).
Ackerman et al., Arch. Neurol. 38:537–43 (1981).
Gur et al., Invest. Radiol. 20:672–677 (1985).

(List continued on next page.)

Primary Examiner—Richard L. Raymond
Assistant Examiner—Gary E. Hollinden
Attorney, Agent, or Firm—Lyon & Lyon

[57] ABSTRACT

The invention provides a method of detecting blood flow abnormality or variation in a human or non-human body, said method comprising administering into the cardiovascular system of a said body a contrast enhancing amount of an intravascular paramagnetic metal containing magnetic resonance imaging contrast agent, subject said body to a magnetic resonance imaging procedure capable of generating from magnetic resonance signals from said body a series of temporally spaced images of at least a part of said body into which said agent passes, and detecting temporal variations in said signals or images whereby to identify regions of abnormal or modified blood flow in said body and to indicate the degree of blood flow abnormality or modification therein.

36 Claims, No Drawings

OTHER PUBLICATIONS

Kucharczyk et al., Radiology 179:221–227 (1991).
Moseley, et al., Acta Neurochirurgica 51:207–209 (1990).
Baker et al., AJR 156:1133–1143 (1991).
Moseley et al., Topics in Magn. Reson. Imaging 3:50–67 (1991).
Ordidge et al., Mag. Res. Med. 10:227–240 (1989).
White et al., SMRM 10, Aug. 1991.
Moseley et al., Journal of the Canadian Association of Radiologists 42:31–38 (1991).
Rocklage et al., Investigative Radiology, (1990) 25:537–538.
Vexier et al., RSNA abstract (Annual Meeting) (1991).
Vexler et al., RSNA Works in Progess (1991).
Asgari, et al., SMRM Annual Meeting, Aug. 1991.
Kucharczyk et al., Acta Neurochirurgica 51:254–258 (1990).
Moseley et al., Proc. Western Neuroradiologic Soc. (1989): Paper 34.

METHODS FOR DETECTING BLOOD PERFUSION VARIATIONS BY MAGNETIC RESONANCE IMAGING

FIELD OF THE INVENTION

This invention relates to improvements in and relating to in vivo proton magnetic resonance imaging, in particular imaging of phenomena associated with blood flow variations and abnormalities. This invention is particularly useful in the determination of the extent and severity of ischemia.

BACKGROUND OF THE INVENTION

Magnetic resonance imaging (MRI) has been used successfully to study blood flow in vivo. Moreover Villringer et al., Magnetic Resonance in Medicine 6:164-174 (1988), Cacheris et al. Society of Magnetic Resonance in Medicine, 7th Annual Meeting, San Francisco, 1988 (SMRM 1988) Works in Progress, page 149 and Belliveau et al., SMRM 1988, Book of Abstracts, page 222 have proposed the use of certain paramagnetic lanthanide chelates as magnetic susceptibility, that is $T_2^*$ shortening, MRI contrast agents for studies of cerebral blood flow.

Unlike many previous imaging procedures, $T_2$ or $T_2^*$-weighted MRI using magnetic susceptibility (MS) contrast agents (hereinafter MS imaging) enabled blood perfusion deficits, e.g., cerebral ischemia, to be visualized rapidly as the MR signal intensity was reduced in the regions of normal perfusion due to the effect of the contrast agent, with ischemic tissue being revealed by its retention of signal intensity.

Blood perfusion deficits are associated with several serious and often life-threatening conditions. Rapid identification and localization of such deficits is highly desirable in order that the appropriate corrective action, be it therapeutic or surgical, may be taken promptly. Thus in the case of cerebral ischemia for example any delay in post-ischemic recirculation and reoxygenation of brain tissue reduces neuronal survivability.

MS imaging therefore represents a major improvement over routine $T_2$ or $T_2^*$-weighted imaging in the absence of MS contrast agents since in the routine procedures ischemia or infarcts only become detectable 2 to 3 hours after the event, e.g., a stroke, which gave rise to the perfusion deficit. However, while determination of the existence and location of a perfusion deficit is important, it is also desirable to be able to detect the degree or severity, and if possible the onset and duration, of blood flow abnormalities or variations in a quantifiable manner and we now propose that this be done using a modified MS imaging procedure.

SUMMARY OF THE INVENTION

Viewed from one aspect the invention provides a method of detecting blood flow abnormality or variation in a human or nonhuman, especially mammalian, body, said method comprising administering into the cardiovascular system of a said body a contrast enhancing amount of an intravascular paramagnetic metal, e.g., transition metal or lanthanide, containing magnetic resonance imaging contrast agent, subjecting said body to a magnetic resonance imaging procedure capable of generating from magnetic resonance signals from said body a series of temporally spaced images of at least a part of said body into which said agent passes, and detecting temporal variations in said signals or images whereby to identify regions of abnormal or modified blood flow in said body and to indicate the degree of blood flow abnormality or modification therein.

Thus the method of the invention provides a quantitative and temporal determination of local perfusion variations, e.g., deficits or increases, which may arise from, for example, stroke, microsurgery or administration of blood flow modifying pharmaceuticals.

The method of the present invention is especially preferably carried out using a so-called fast or ultra fast imaging technique in order to enable a series of $T_2^*$ dependent images to be generated with as short as possible a time interval between successive images. For this reason, techniques capable of generating images with time intervals of less than 5 seconds, especially less than 0.5 seconds and more especially less than 100 milliseconds, are particularly preferred. Thus techniques such as spin echo, gradient echo, TurboFLASH and most especially the various varieties of echo planar imaging (EPI) are particularly suitable for use in accordance with the method of the invention.

The contrast agent used according to the method of the invention should be an intravascular contrast agent, that is to say one which is substantially retained within the cardiovascular system at least until it has passed through the body region or organ of particular interest. Generally therefore blood pooling, particulate and hydrophilic contrast agents or contrast agents possessing more than one of these properties are of particular interest.

Besides its obvious application in terms of identifying and providing an indication of the severity of cerebral or coronary ischemias or infarcts, the method of the present invention has a broad range of possible diagnostic and evaluative applications of which the following list names but a few:

Assessment of the impact of induced brain hypothermia on cerebral perfusion during neurosurgery for stroke;

Assessment of the effects of aging on cerebral perfusion including the study of the etiology of lacunar infarcts;

Assessment of the effects of cocaine, amphetamine and ethanol on cerebral perfusion in mildly and severely ischemic brain;

Definition of the "therapeutic window" in reversible focal ischemia for heparin, vasodilators, antihypertensives and calcium antagonists;

Study of the relationship between blood ammonia, lactate, pH and cerebral perfusion in cerebral ischemia associated with acute liver failure (this has implications for the treatment of Alzheimer's disease);

Assessment of cerebral perfusion in brain dysfunction associated with acute severe symptomatic hyponatremia;

Evaluation of new therapies (for example thrombolytic therapies and clot removal, calcium channel blockers, anti-inflammatory agents, angioplasty, etc.) in the treatment of cerebral vasospasm;

Assessment of cerebral perfusion following induced subarachnoid hemorrhage;

Localization and assessment of thrombus and plaque;

Evaluation of new therapies for stroke (for example t-PA, aspirin, antiphospholipids/lupusanticoagulants, antiphospholipid antibodies, etc.);

Evaluation of risk factors for stroke (for example elevated serum lipids, etc.);

Assessment of different degrees of ischemia in large tissue masses; and

Monitoring of other induced vasodilatory effects.

Thus viewed from a further aspect the invention provides a method of detecting and quantitatively evaluating the severity of ischemia in a human or non-human, especially mammalian, body, said method comprising administering into the cardiovascular system of said body a contrast enhancing amount of an intravascular paramagnetic metal containing magnetic susceptibility magnetic resonance imaging contrast agent, subjecting said body to a magnetic resonance imaging procedure capable of generating from magnetic resonance signals from said body a series of temporally spaced images of at least a part of said body into which said agent passes, and detecting temporal variations in said signals or images whereby to detect ischemic tissue and to provide a quantitative indication of the degree of blood perfuson deficit therein.

Viewed from a still further aspect, the present invention also provides a method of monitoring the vasodilatory or vasoconstrictive effects of a physiologically active substance administered to a human or non-human animal body, for example a calcium antagonist, said method comprising administering said substance into said body, administering into the cardiovascular system of said body a contrast enhancing amount of an intravascular paramagnetic metal containing magnetic susceptibility magnetic resonance imaging contrast agent, subjecting said body to a magnetic resonance imaging procedure capable of generating from magnetic resonance signals from said body a series of temporally spaced images of at least a part of said body into which said agent passes, and detecting temporal variations in said signals or images whereby to monitor the vasoconstriction or vasodilation induced by said substance.

Viewed from a still further aspect, the present invention also provides a method of monitoring surgically induced blood perfusion variations, either before or during surgery, said method comprising administering a contrast enhancing amount of an intravascular paramagnetic metal containing magnetic susceptibility magnetic resonance imaging contrast agent into the cardiovascular system of a human or animal body which is undergoing or has undergone surgery, in particular microsurgery on said cardiovascular system, subjecting said body to a magnetic resonance imaging procedure capable of generating from magnetic resonance signals from said body a series of temporally spaced images of at least a part of said body into which said agent passes, and detecting temporal variations in said signals or images whereby to identify regions of surgically induced variations in blood perfusion.

Viewed from a still further aspect the invention provides the use of a MS contrast agent for the manufacture of a contrast medium for use in the methods of the invention.

DETAILED DESCRIPTION OF THE INVENTION

The magnetic susceptibility, $T_2^*$-reducing effect of MS contrast agents is to a large degree dependent on the magnitude of the magnetic moment of the magnetic species within the contrast agent—the higher the magnetic moment the stronger the effect. Indeed, the effect is approximately proportional to the square of the magnetic moment, making the effect of Dy(III) about 1.8 times larger than that of Gd(III). In general, paramagnetic metal species having magnetic moments of $\geq 4$ Bohr Magnetons (BM) will be preferred. The contrast agents particularly preferred for use in the method of the present invention are those containing paramagnetic lanthanide ions, especially high spin lanthanides such as ions of Dy, Gd, Eu and Ho, in particular Dy(III).

In order that they may be administered at effective but non-toxic doses, such paramagnetic metals will generally be administered in the form of ionic or much more preferably non-ionic complexes, especially chelate complexes, optionally bound to larger carrier molecules which may be selected to enhance the blood pooling nature of the contrast agent or to reduce the osmolality of the contrast medium by increasing the number of paramagnetic centers per contrast agent molecule (or molecular ion).

A wide range of suitable chelants, polychelants, and macromolecule-bound chelants for paramagnetic metal ions has been proposed in the patent literature over the last decade and in this respect particular regard may be had to US-A-4687659 (Quay), US-A-4647447 (Gries), US-A-4639365 (Sherry), EP-A-186947 (Nycomed), EP-A-299795 (Nycomed), WO-A-89/06979 (Nycomed), EP-A-331616 (Schering), EP-A-292689 (Squibb), EP-A-232751 (Squibb), EP-A-230893 (Bracco), EP-A-255471 (Schering), EP-A-277088 (Schering), EP-A-287465 (Guerbet), WO-A-85/05554 (Amersham) and the documents referred to therein, the disclosures of all of which are incorporated herein by reference.

Particularly suitable chelants for the formation of paramagnetic metal chelate MS contrast agents for use in the method of the present invention include the following: N,N,N',N'',N''-diethylenetriaminepentaacetic acid (DTPA), 6-carboxymethyl-3,9-bis(methylcarbamoylmethyl)-3,6,9-triazaundecanedioic acid (DTPA-BMA), 6-carboxymethyl-3,9-bis(morpholinocarbonylmethyl)-3,6,9-triazaundecanedioic acid (DTPA-BMO), 1,4,7,10-tetraazacyclododecane-N,N',N'',N'''-tetraacetic acid (DOTA), 1,4,7,10-tetraazacyclododecane-N,N',N''-triacetic acid (D03A), 1-oxa-4,7,10-triazacyclododecane-N,N',N''-triacetic acid (OTTA), polylysine-bound DTPA and DTPA derivatives (DTPA-polylysine), polylysine-bound DOTA and DOTA derivatives (DOTA-polylysine), soluble dextran-bound DTPA and DTPA derivatives having with a total molecular weight $\geq 40$ KD, preferably in the range 60–100 KD (DTPA-dextran).

Particularly suitable paramagnetic metal ions for chelation by such chelates are ions of metals of atomic numbers 21 to 29, 42, 44 and 57 to 71, especially 57 to 71, more especially Cr, V, Mn, Fe, Co, Pr, Nd, Eu, Gd, Tb, Dy, Ho, Er, Tm, Yb and Ln, in particular Cr(III), Cr(II), V(II), Mn(III), Mn(II), Fe(III), Fe(II) and Co(II) and especially Gd(III), Tb(III), Dy(III), Ho(III), Er(III) and Tm(III) and Yb(III), more particularly Dy(III), Ho(III) and Er(III).

All paramagnetic ions have both $T_1$ and $T_2$-reducing effects on the surrounding non-zero spin nuclei: $T_1$ reduction leads to image intensity increases whereas $T_2$ reduction leads to image intensity losses. For the purposes of the present invention it is particularly preferred to use paramagnetic metals which have relatively poor or even negligible $T_1$-relaxivity in order to maximize the MR effect of the contrast agents in $T_2^*$ or $T_2$-weighted MR imaging. Thus Dy(III) or even Yb(III) would generally be used in preference to Gd(III).

In order to perform the method of the invention with as high as possible a safety factor (the ratio between the dose of the contrast agent and its $LD_{50}$), it is particularly preferred to use non-ionic or low osmolality chelates, i.e., chelates which carry no overall ionic charge, such as DyDTPA-BMA for example, or in which the complex has an overall ionic charge to paramagnetic metal center ratio of 1.5 or less.

Furthermore, to ensure that the contrast agent remains wholly or essentially within the blood vessels during passage through the body region of interest, the contrast agent will as mentioned above preferably be particulate, hydrophilic or blood-pooling.

Examples of suitable blood-pooling agents include the inert soluble macromolecule-bound chelates of the type described by Nycomed in EP-A-186947 and WO-A-89/06979. Binding the chelant to a macromolecule, e.g., a polysaccharide such as dextran or derivatives thereof, to produce a soluble macromolecular chelant having a molecular weight above the kidney threshold, about 40 KD, ensures relatively long term retention of the contrast agent within the cardiovascular system.

Examples of suitable hydrophilic contrast agents include linear, branched or macrocyclic polyaminopolycarboxylic acid chelates of paramagnetic metal ions, and also especially include chelates of chelants in which one or more carboxylic acid groupings are replaced by other groups, such as amides, esters or hydroxamates, as well as such chelants in which the chelant backbone is substituted by hydrophilic groupings such as for example hydroxyalkyl or alkoxyalkyl groups. Chelants of these types are disclosed for example in US-A-4,687,658 (Quay), US-A-4,687,659 (Quay), EP-A-299795 (Nycomed) and EP-A-130934 (Schering).

Particular mention in this regard must be made of the Dy(III), Ho(III) and Er(III) chelates of DTPA-BMA, DTPA-BMO and D03A.

The dosages of the contrast agent used according to the method of the present invention will vary according to the precise nature of the contrast agent used. Preferably however the dosage should be kept as low as is consistent with still achieving an image intensity reduction in $T_2^*$-weighted imaging. Thus for Dy(III) based chelates, for example, dosages of Dy of 0.05 to 0.5 mmol/kg bodyweight, and especially 0.08 to 0.3 mmol/kg, are particularly preferred. In this way not only are toxicity-related problems minimized but the sensitivity of the imaging method towards the detection of ischemia of varying degrees of severity is increased. At higher dosages the signal suppression by the MS contrast agent may be unduly abrupt and intense, making regions with relatively minor perfusion deficits appear to have the characteristics of relatively normal blood flow. For most MS contrast agents the appropriate dosage will generally lie in the range 0.02 to 3 mmol paramagnetic metal/kg bodyweight, especially 0.05 to 1.5 mmol/kg, particularly 0.08 to 0.5, and more especially 0.1 to 0.4 mmol/kg. It is well within the skill of the average practitioner in this field to determine the optimum dosage for any particular MS contrast agent by simple experiment, either in vivo or in vitro.

Where the contrast agent is ionic, such as is the case with DyDTPA, it will conveniently be used in the form of a salt with a physiologically acceptable counterion, for example an ammonium, substituted ammonium, alkali metal or alkaline earth metal cation or an anion deriving from an inorganic or organic acid. In this regard, meglumine salts are particularly preferred.

Contrast agents may be formulated with conventional pharmaceutical or veterinary aids, for example, stabilizers, antioxidants, osmolality adjusting agents, buffers, pH adjusting agents, etc., and may be in a form suitable for injection or infusion directly or after dispersion in or dilution with a physiologically acceptable carrier medium, e.g. water for injections. Thus the contrast agents may be formulated in conventional administration forms such as powders, solutions, suspensions, dispersions etc., however solutions, suspensions and dispersions in physiologically acceptable carrier media will generally be preferred.

The contrast agents may therefore be formulated for administration using physiologically acceptable carriers or excipients in a manner fully within the skill of the art. For example, the compounds optionally with the addition of pharmaceutically acceptable excipients, may be suspended or dissolved in an aqueous medium, with the resulting solution or suspension then being sterilized. Suitable additives include, for example, physiologically biocompatible buffers (as for example DTPA or DTPA-bisamide (e.g. 6-carboxymethyl-3,9-bis(methylcarbamoylmethyl) -3,6,9-triazaundecanedioic acid)) or calcium chelate complexes (as for example salt forms of the calciumDTPA complex or the calcium DTPA-bisamide complex, such as NaCaDTPA-bisamide) or, optionally, additions (e.g. 1 to 50 mole percent) of calcium or sodium salts (for example, calcium chloride, calcium ascorbate, calcium gluconate or calcium lactate and the like).

Parenterally administrable forms, e.g., intravenous solutions, should of course be sterile and free from physiologically unacceptable agents, and should have low osmolality to minimize irritation or other adverse effects upon administration and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are coppatible with the contrast agents and which will not interfere with the manufacture, storage or use of products.

In the method of the present invention where the paramagnetic metal has any significant $T_1$-reducing effect, which is especially the case where the paramagnetic metal is Gd rather than Dy, this $T_1$-reducing effect may also be utilized to increase the degree of certainty with which perfused regions are identified by generating corresponding $T_1$ weighted images and determining the signal ratio for each pixel/voxel between the two types of image. In this way tissue with severe hypoperfusion might be distinguished from tissue in which blood flow has ceased entirely. Where such a technique is used however it will be especially desirable to use the low toxicity, low osmolality forms of the paramagnetic metal complex in order to operate with as large a safety factor as possible. Thus for Gd it will generally be preferable to use GdD03A, GdDTPA-BMA or GdDTPA-BMO rather than GdDTPA salts.

Generally data manipulation forms a useful part of the method of the invention, since information regarding the severity of perfusion deficit may be extracted from the rate and degree of signal intensity loss which takes place for the region of interest following MS contrast agent administration (the less severe the tissue hypoperfusion, the greater the loss of signal intensity) and from the duration and magnitude of signal loss. Comparison with data obtained for healthy tissue enables a form of perfusion calibration to be made. Moreover indications of the blood volume affected may also be obtained by measurement of the area under the curve for a plot of pixel/voxel signal intensity loss over time for the duration of the MS contrast agent-induced signal loss. The necessary data manipulation, including display of zones of reduced or enhanced perfusion optionally superimposed on a selected background image, e.g., the "native" image obtained in the absence of the MS contrast agent, can of course be performed by a computer, generally the same computer as is arranged to operate the MR imager and generate MR images from the detected MR signals.

The method of the invention will now be described further by way of example with particular reference to certain nonlimiting embodiments.

Young adult cats weighing 2.0 to 4.5 kg were anesthetized with 30 mg/kg i.v. Nembutal. Polyethylene catheters were placed in the femoral artery and vein for blood pressure monitoring and drug administration. The right middle cerebral artery (MCA) was isolated via transorbital approach and occluded just proximal to the origin of the lateral striate arteries with bipolar electrocautery followed by complete surgical transsection. The dural incision and orbit were covered with saline-moistened gauze and absorbable gelatin sponge.

A General Electric CSI (2 Tesla) unit, equipped with Acustar S-150 self-shielded gradient coils ($\pm 20$ gauss/cm, 15 cm bore size) was used. MRI was performed with an 8.5 cm inner-diameter low-pass birdcage proton imaging coil. Successive multislice $T_2$-weighted coronal images were obtained for up to 12 hours following occlusion. $T_2$-weighted images (TR 2800, TE 80 and 160, 3 mm slices, 1 mm gap) were obtained with a field-of-view (FOV) of 80 mm in which two scans were averaged for each one of the 128 phase-encoding steps resulting in a total acquisition time of 12 minutes.

In order to evaluate the anatomic region of perfusion deficiency following MCA occlusion, cats were injected with a non-ionic $T_2^*$-shortening contrast agent, DyDTPA-BMA. The DyDTPA-BMA complex was prepared by refluxing an aqueous suspension containing stoichiometric amounts of dysprosium oxide and DTPA-BMA. BMA. The contrast agent was infused i.v. at doses of 0.25, 0.5 or 1.0 mmol/kg. For the 0.5 mmol/kg dose, administration was started at phase-encoding step #32 and finishing at step #60 (approximately 3 min) of $T_2$-weighted image acquisition. DyDTPABMA injections were given at different time points post MCA occlusion in individual cats. After injection, the magnetic susceptibility effect was quantified for up to 60 minutes in both ischemic and normal hemispheres by comparing region-of-interest (ROI) intensity to pre-contrast $T_2$-weighted ROI intensities. ROI image analyses were carried out in the ischemic inferior parietal gyrus, caudate/putamen, and internal capsulate, and compared with the corresponding uninjured contralateral regions. A signal intensity ratio was calculated as the ROI image intensity ratio of an abnormal, ischemic region over that of the normal, contralateral side. Results were expressed as the mean percentage change $\pm$ Standard Error of the Mean ($\overline{X} \pm$ S.E.M.).

At the conclusion of the MR protocol, 15 ml/kg of a 2% solution of 2,3,5-triphenyl tetrazolium chloride (TTC) was infused transcardially. The brain was removed from the cranium after 10–20 minutes, immersed in a 2% TTC solution for another 0–20 minutes, and then stored overnight in 10% buffered formalin in a light shielded container. 24–36 hours later the brain was sectioned coronally at 2–3 mm and immediately examined for histologic evidence of ischemic damage, as evidenced by pallor of TTC staining.

Using a 0.5 mmol/kg dosage of DyDTPA-BMA, maximum signal intensity losses of 35% were observed in the gray matter of the normal non-occluded cerebral hemisphere during the first 15 minutes after injection. Signal intensity changes in white matter (internal capsule) in both the normal and ischemic hemispheres were smaller than in gray matter, presumably because of higher cerebral blood flow to gray matter. The resulting contrast-enhanced images had superior gray/white matter contrast than $T_2$-weighted spin-echo MR images without contrast. At 45 minutes after administration of DyDTPA-BMA, signal intensity had recovered to at least 90% of pre-contrast control values in all cerebral tissues. Increasing the dosage of DyDTPA-BMA from 0.5 to 1.0 mmol/kg produced only a minimal difference in immediate post-contrast signal intensity. Long TE times (160 msec) produced the highest gray/white matter contrast after DyDTPA-BMA at each of the 3 doses tested. (In general, in the method of the invention, using higher TE values leads to a slight loss in signal-to-noise ratio but it also improves sensitivity to $T_2^*$ and hence to the MS contrast agent).

Perfusion deficits resulting from occlusion of the MCA were detected as regions of signal hyperintensity of the occluded ischemic tissue compared to the normally perfused areas in the contralateral hemisphere. Relative hyperintensity was found in the occluded basal ganglia as early as 30 minutes post-occlusion for both the 1 mmol/kg and 0.5 mmol/kg dosages. Signal differences between ischemic and contralateral control tissues were observed for gray matter in the inferior parietal gyrus (42 $\pm$14%), and basal ganglia (26$\pm$8%), and to a lesser extent, for the white matter in the internal capsule (5$\pm$4%). By comparison, $T_2$-weighted MRI without contrast failed to demonstrate any significant signal differences prior to approximately 2–3 hours post MCA occlusion (see Table 1). As well, DyDTPA-BMA administration allowed detection of small developing infarcts that were not visible or were ambiguous on $T_2$-weighted images without contrast (see Table 2).

TABLE 1

Effect of DyDTPA-BMA administration on the time of detection of cerebral ischemic damage.

| Dose DyDTPA-BMA (mmol/kg) | # Cats Tested | Onset of signal hypertensity (relative to pre-contrast $T_2$-weighted MRI) | | |
|---|---|---|---|---|
| | | Earlier | Same Time | Later |
| 0.25 | 5 | 1 | 4 | 0 |
| 0.50 | 16 | 12 | 4 | 0 |
| 1.0 | 6 | 4 | 2 | 0 |

TABLE 2

Effect of DyDTPA-BMA administration on the definition of injury site (signal intensity ratio of injured tissue to corresponding contralateral control tissue) compared to pre-contrast $T_2$-weighted image.

| Dose DyDTPA-BMA (mmol/kg) | # injections contrast | Signal intensity ratio (relative to pre-contrast $T_2$-weighted image) | | |
|---|---|---|---|---|
| | | Better | Same | Worse |
| 0.25 | 5 | 4 | 1 | 0 |
| 0.50 | 23 | 17 | 6 | 0 |
| 1.0 | 16 | 14 | 2 | 0 |

Within 3-5 hours after MCA occlusion, $T_2$-weighted images also demonstrated tissue injury clearly, including increased mass-effect and hyperintensity (edema) throughout the MCA territory. The distribution of increased signal intensity correlated well anatomically with regions of perfusion deficiency demonstrated with DyDTPA-BMA-enhanced MR imaging. A continuing close anatomic correspondence between areas of perfusion deficit and edematous regions was seen 9 hours and 11 hours post occlusion. In subsequent TTC-stained coronal sections, these areas were found to exhibit characteristics typical of ischemic tissue injury, such as pallor of staining, coagulation necrosis, and glial proliferation.

These results confirm that MS contrast agent enhanced MRI can significantly advance the time of detection of cerebral ischemic insults. Evidence of stroke-induced perfusion deficits was observed in the MCA territory as early as 45 minutes post-occlusion using contrast-enhanced MRI, whereas $T_2$-weighted spin-echo images without contrast did not demonstrate increased signal intensity until 2-3 hours after occlusion.

Contrast in $T_2$-weighted spin-echo MRI can be produced by changes in the microscopic magnetic fields experienced by protons undergoing molecular diffusion. These field gradients cause spin dephasing and loss of spin echo signal intensity. Field gradients arise at the interface of two volumes with different magnetic susceptibilities and thus different induced magnetic fields.

The presence of paramagnetic chelates can alter the magnetic susceptibility of tissue. In the brain, since the chelates are confined to the intravascular space by the blood-brain barrier, a field gradient is induced between the capillary space and surrounding (perfused) tissue resulting in significant signal loss. These results show that this approach to MR contrast enhancement can be used to differentiate ischemic from normally perfused regions.

A further notable advantage of the method of the invention is its relative insensitivity to motion compared to diffusion-weighted MR imaging. Given the relatively high safety index of DyDTPA-BMA ($LD_{50}$ i.v. administration in mice is 34 mmol/kg), the long duration of the magnetic susceptibility effect makes this a particularly good MS contrast agent for use with $T_2$-weighted MRI.

The contrast-enhanced images suggested considerable regional heterogeneity in perfusion throughout the ischemic MCA territory. Post-contrast signal hyperintensity was observed earlier in the basal ganglia than the neocortex. This finding suggests that non-anastomosing end-arterial tissues, such as the caudate and putamen, are most susceptible to post-ischemia perfusion deficits, since no collateral circulation is available. In collaterally perfused areas such as neocortex, on the other hand, tissue injury may be mitigated somewhat by continued blood flow in the partially ischemic watershed regions. It seems likely that the method of the invention may be able to help identify reversibly ischemic penumbra from infarcted tissue based on the degree and duration of perfusion deficit to cerebral tissues.

In further studies of cerebral perfusion deficits on a MCA model described above, using echo planar imaging in conjunction with low, 0.1 mmol/kg, doses of DyDTPA-BMA, we have found that quantitative spatial and temporal assessment of stroke affected tissue may be made. This dosage reduction further increases both the potential sensitivity and the safety profile of the method of the invention.

The advantage of using echo planar MRI with a MS contrast agent is that images may be acquired continuously before, during and after contrast injection. This allows the time course of the contrast agent passage through a tissue to be monitored and to obtain images at the maximum contrast dosage.

Echo planar images on the GE CSI 2 Tesla were acquired in a sequential fashion. Sixteen images were obtained one each second or less, each image possessing a 66 msec acquisition time with a data matrix of $64 \times 64$ pixels over a $60 \times 60$ mm field-of-view. The slice thickness was 3 mm. The echo-planar sequence was that of a gradient-echo nature, with the time of echo (TE) value adjusted to maximize the $T_2^*$-shortening contrast effect.

What is claimed is:

1. A method of detecting regions of blood flow abnormality or variation in a human or non-human body, said method comprising the steps of (1) administering into the cardiovascular system of said body a contrast enhancing amount of a paramagnetic metal containing magnetic resonance imaging contrast agent, (2) subjecting said body to a magnetic resonance imaging procedure and obtaining a series of temporally spaced magnetic resonance signals or images from regions in at least a part of said body into which said agent passes, (3) detecting temporal variations in said signals or images, and (4) identifying from said temporal variations in said signals or images regions of abnormal or modified blood flow in said body and providing a quantitative indication of the degree of blood flow abnormality or modification therein.

2. A method of detecting and quantitatively evaluating the severity and spatial extent of ischemic regions in a human or non-human body, said method comprising the steps of (1) administering into the cardiovascular system of said body a contrast enhancing amount of a paramagnetic metal containing magnetic susceptibility magnetic resonance imaging contrast agent, (2) subjecting said body to a magnetic resonance imaging procedure and obtaining a series of temporally spaced magnetic resonance signals or images from regions in at least a part of said body into which said agent passes, (3) detecting temporal variations in said signals or images, and (4) detecting from said temporal variations in said signals or images ischemic tissue and providing a quantitative and spatial indication of the degree of blood perfusion deficit therein.

3. A method according to claim 1 wherein said contrast agent comprises a physiologically tolerable chelate complex of a paramagnetic lanthanide ion or a physiologically tolerable salt of such a chelate.

4. A method according to claim 3 wherein said contrast agent is a chelate complex of a lanthanide, or a physiologically tolerable salt thereof.

5. A method according to claim 4 wherein said contrast agent is a chelate complex of a metal ion selected from the group consisting of the paramagnetic ions of Yb, Tm, Dy, Ho, Er and Gd, or a physiologically tolerable salt thereof.

6. A method according to claim 5 wherein said contrast agent is a chelate complex of Dy(III) or a physiologically tolerable salt thereof.

7. A method according to claim 4 wherein said contrast agent comprises a physiologically tolerable nonionic paramagnetic chelate complex.

8. A method according to claim 7 wherein said contrast agent comprises a physiologically tolerable nonionic Dy(III) paramagnetic chelate complex.

9. A method according to claim 3 wherein said chelate complex is a complex of a linear, branched or macrocyclic chelant selected from polyaminopolycarboxylic acid chelants and from chelants wherein one or more carboxylic acid groupings are replaced with an amide, ester or hydroxamate grouping.

10. A method according to claim 9 wherein said chelate complex is a complex of a chelant selected from the group consisting of DTPA, DTPA-BMA, DOTA, DO3A -and DTPA-BMO.

11. A method according to claim 5 wherein said chelate complex is a complex of a chelant selected from the group consisting of DTpA, DTpA-BMA, DOTA, DO3A, DTPA-BMO.

12. A method according to claim 11 wherein said chelate complex is DyDTPA-BMA.

13. A method according to claim 3 wherein said contrast agent is administered at a dosage of 0.02 to 3 mmol/kg bodyweight.

14. A method according to claim 13 wherein said contrast agent is administered at a dosage of 0.08 to 0.5 mmol/kg.

15. A method according to claim 1 wherein said magnetic resonance imaging procedure is a fast imaging procedure.

16. A method according to claim 15 wherein said procedure is one having an image acquisition time of less than 5 seconds.

17. A method according to claim 16 wherein said procedure is one having an image acquisition time of less than 0.5 seconds.

18. A method according to claim 17 wherein said procedure is an echo planar imaging procedure.

19. A method according to claim 1 comprising generating temporally spaced $T_2^*$ or $T_2$-weighted images.

20. A method according to claim 19 wherein said magnetic resonance imaging procedure is a spin-echo or gradient echo procedure.

21. A method according to claim 19 comprising generating and comparing $T_1$-weighted images or signals transformable thereto and $T_2^*$ or $T_2$-weighted images or signals transformable thereto whereby to identify body regions in which blood perfusion occurs.

22. A method according to claim 1 being a method of detecting body regions of blood flow deficit.

23. A method according to claim 22 being a method of detecting ischemic regions.

24. A method according to claim 1 wherein said contrast agent comprises a physiologically tolerable complex of a paramagnetic transition metal ion or a physiologically tolerable salt of such a chelate.

25. The method of claim 1 wherein said magnetic resonance imaging contrast agent contains as a said metal a species having a magnetic moment of at least 4 Bohr magnetons.

26. The method of claim 1 wherein said magnetic resonance imaging agent contains as a said metal a transition metal selected from Cr, V, Mn, Fe and Co.

27. The method of claim 1 wherein said magnetic resonance imaging agent contains as a said metal a lanthanide selected from Gd, Tb, Dy, Ho, Er, Tm and Yb.

28. The method of claims 1 or 2 comprising the further step of obtaining a quantitative indication of the blood volume in said regions affected by said blood flow abnormality or modification.

29. The method of claim 28 comprising the further step of numerically evaluating the area under a curve of a plot of signal intensity change over time.

30. The method of claims 1 or 2 comprising the further steps of subjecting said body to a magnetic resonance imaging procedure in the absence of said contrast agent and obtaining a magnetic resonance signal or image from at least a part of said body to establish a native signal or image, and wherein temporal variations are detected between said native signal or image and said temporally spaced series of signals or images obtained in the presence of said contrast agent.

31. The method of claim 1 comprising the further step of detecting rates of signal intensity changes in said temporally spaced signals or images.

32. The method of claim 1 comprising the further step of detecting degrees of signal intensity changes in said temporally spaced signals or images.

33. The method of claim 32 comprising the further step of detecting durations of signal intensity changes in said temporally spaced signals or images.

34. The method of claims 1 or 2 wherein said step of obtaining a series of temporally spaced magnetic resonance signals or images further comprises obtaining signals or images from regions of normally perfused tissue in at least a part of said body to establish a reference perfusion signal or image.

35. The method of claims 1 or 2 wherein said part of said body is within the cranium.

36. The method of claims 1 or 2 wherein said part of said body is a cardiac region.

* * * * *